United States Patent [19]
Taylor et al.

[11] Patent Number: 5,935,107
[45] Date of Patent: Aug. 10, 1999

[54] APPARATUS AND METHOD FOR SURGICALLY ACCESSING A BODY CAVITY

[75] Inventors: Scott Taylor, Mission Viejo; Charles C. Hart, Huntington Beach, both of Calif.

[73] Assignee: Applied Medical Resources Corporation, Laguna Hills, Calif.

[21] Appl. No.: 08/726,615

[22] Filed: Oct. 7, 1996

[51] Int. Cl.⁶ .................................................. A61B 17/00
[52] U.S. Cl. .......................................... 604/164; 604/174
[58] Field of Search .................................. 604/104–109, 604/164, 174, 175; 606/191–198

[56] References Cited

U.S. PATENT DOCUMENTS

| | | |
|---|---|---|
| Re. 34,021 | 8/1992 | Mueller et al. . |
| 5,002,557 | 3/1991 | Hasson ........................................ 606/191 |
| 5,071,405 | 12/1991 | Piontek et al. . |
| 5,073,166 | 12/1991 | Parks et al. ........................... 604/174 X |
| 5,122,122 | 6/1992 | Allgood .................................... 604/174 |
| 5,176,697 | 1/1993 | Hasson et al. ............................ 606/191 |
| 5,197,971 | 3/1993 | Bonutti ..................................... 606/192 |
| 5,217,451 | 6/1993 | Freitas ...................................... 604/174 |
| 5,232,451 | 8/1993 | Freitas et al. ............................. 604/174 |
| 5,273,529 | 12/1993 | Idowu ......................................... 604/49 |
| 5,290,249 | 3/1994 | Foster et al. ............................. 604/174 |
| 5,318,012 | 6/1994 | Wilk ...................................... 604/105 X |
| 5,344,420 | 9/1994 | Hilal et al. ............................ 604/164 X |
| 5,549,595 | 8/1996 | Freitas .......................................... 606/1 |
| 5,637,097 | 6/1997 | Yoon ........................................ 604/174 |

*Primary Examiner*—Cary O'Connor
*Assistant Examiner*—Pamela L. Wingood
*Attorney, Agent, or Firm*—Richard L. Myers

[57] ABSTRACT

An access device, such as a gastrostomy tube, includes a Mallincott anchoring structure reinforced with an insert and operable by a pair of sutures. An electrosurgical obturator is positioned in the tube and functions as a stylet for placing the structure in a low profile state. The obturator can then be activated to insert the tube through the abdominal wall and the stomach wall to provide access to the stomach cavity. The sutures can then be tensioned to raise the Mallincott structure to a high profile state and draw the stomach into proximity with the abdominal wall. Removing the obturator leaves the tube operatively disposed and providing direct access to the stomach cavity.

15 Claims, 5 Drawing Sheets

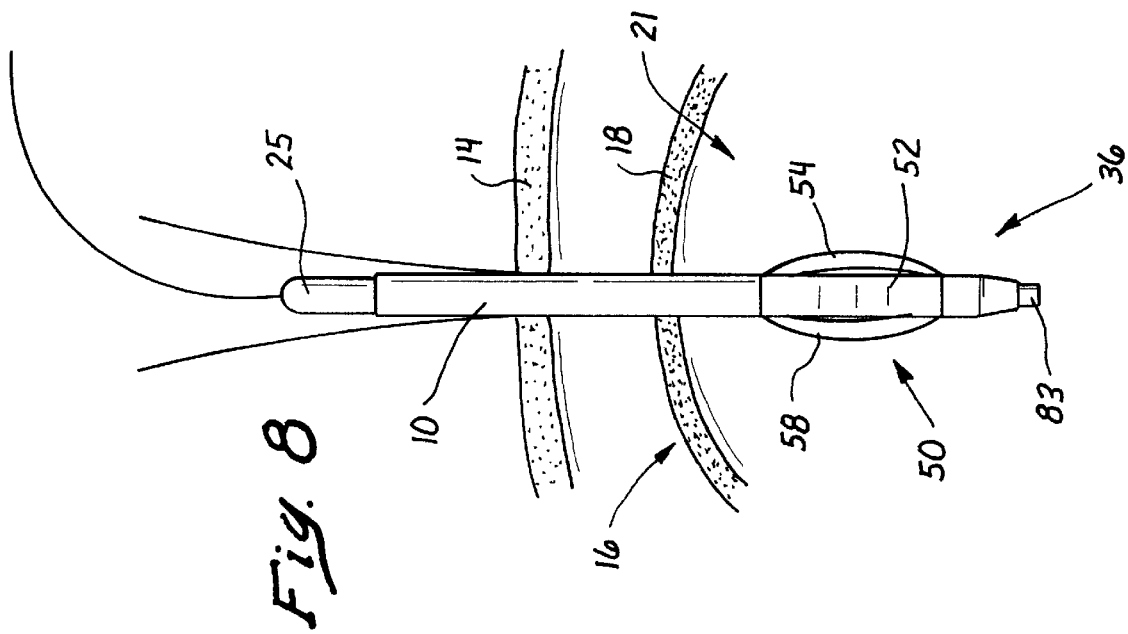
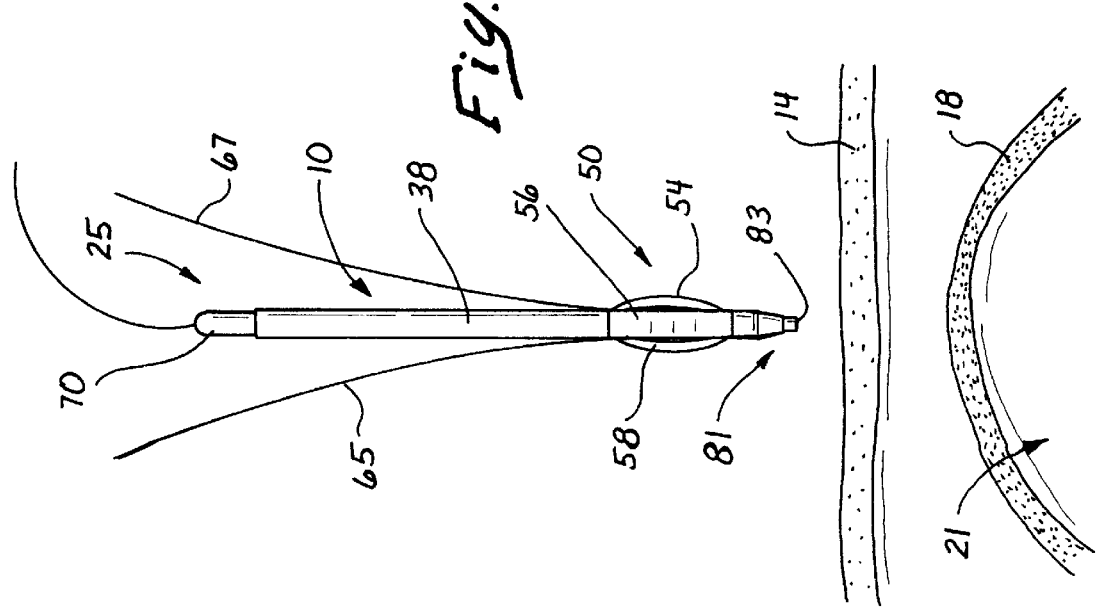

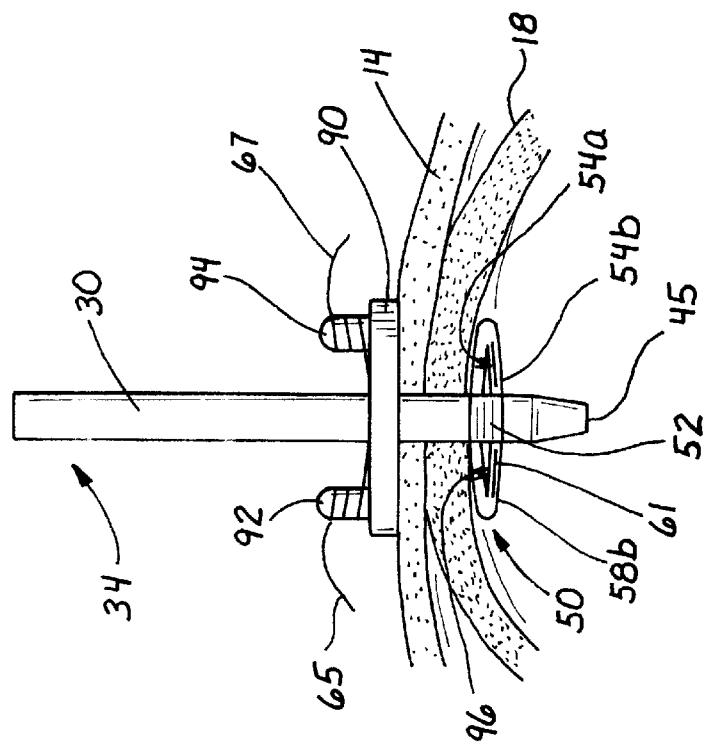
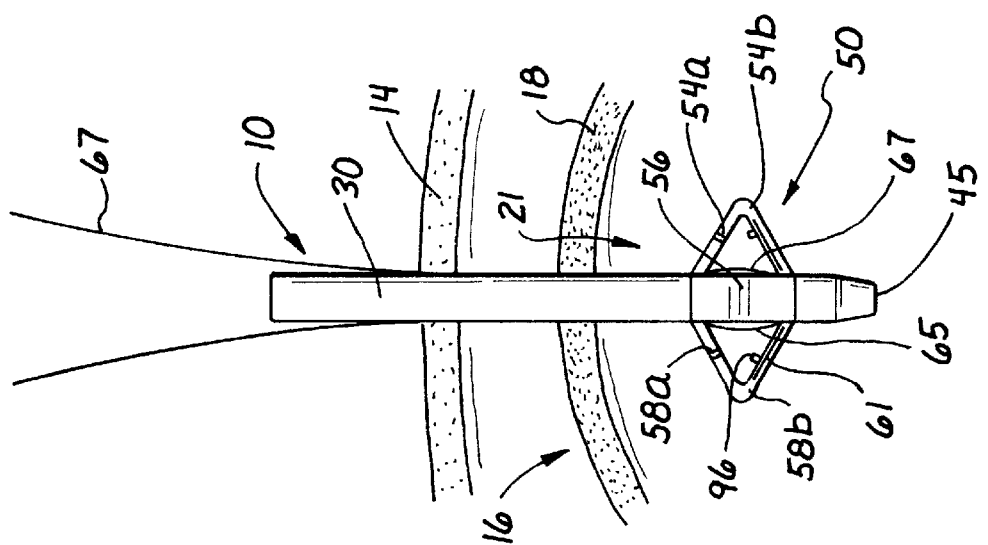

APPARATUS AND METHOD FOR SURGICALLY ACCESSING A BODY CAVITY

BACKGROUND OF THE INVENTION

1. Field of the Invention

This invention relates generally to tubular access devices and more specifically to such access devices which are adapted for disposition across a body wall to provide access into a body cavity.

2. Discussion of the Prior Art

Tubes are used in many surgical procedures to provide access into various body cavities. These tubes are commonly referred to merely as access devices. Illustrative of such a device would be a gastrostomy tube which is adapted for disposition across an abdominal wall and a stomach wall to provide access to a stomach cavity. The lumen or channel of the gastrostomy tube can then be used to introduce food and nutrients directly into the stomach cavity.

In a common gastrostomy procedure such as that disclosed by applicant in U.S. patent application Ser. No. 08/230,165; filed Apr. 19, 1994; and entitled Gastrostomy Apparatus & Method, T-anchors are individually positioned through the abdominal wall and the stomach wall to draw the stomach into proximity with the abdominal wall. With the stomach in this proximate position, a mechanical obturator has been used to position a trocar through the abdominal wall and stomach wall leaving the working channel of the trocar to provide access into the stomach cavity. An elastomeric gastrostomy tube has been provided with a Malecot structure axially stretchable using a mechanical stylet to provide the tube with a low profile. In this configuration, the gastrostomy tube has been inserted through the working channel of the trocar and into the stomach cavity. The trocar and stylet have then been removed leaving the gastrostomy tube to provide access into the stomach cavity.

This procedure, which requires many separate instruments and method steps, is relatively complex. As a consequence, a high level of skill is required in order to ensure that all of the instruments function properly in combination. The time required for the procedure is relatively long greatly increasing the cost of the surgery.

SUMMARY OF THE INVENTION

These problems associated with prior art are overcome with the present invention which primarily includes only two elements, an access device having an anchor which is externally operable, and a obturator which also functions as a stylet. In one embodiment of the concept, the gastrostomy tube is provided with an anchor in the form of a Malecot structure with sutures attached to the distal arms of the structure. An obturator insertable into the gastrostomy tube, can be configured to function as a stylet thereby axially stretching the gastrostomy tube to provide the anchor with a low profile configuration. In this state, the obturator is used to penetrate the abdominal wall and the stomach wall, and to simultaneously move the gastrostomy tube into position. The obturator can then be removed and the anchor expanded by tensioning the sutures within the stomach cavity. Pulling on the sutures and the tube draws the stomach into proximity with the abdominal wall where a fixation member can be coupled to the tube to maintain this operative disposition. Thus these two elements, the gastrostomy tube and the obturator, facilitate placement and operative disposition of the tube without the use of separate T-anchors, a trocar, or a stylet. Accordingly, the operative procedure is very simple, greatly reducing operative time, complexity, and operation costs.

In one aspect of the invention, an access device is adapted for disposition across a body wall and an organ wall defining an organ cavity. An elongate tube having an axis extending between a proximal and a distal end is adapted to extend through the body wall and the organ wall. Apparatus having a fixed relationship with the elongate tube is disposed at the distal end of the tube and is accessible on the proximal side of the body wall for engaging the distal side of the organ wall and for drawing the organ wall into proximity with the body wall.

In an additional aspect of the invention, a gastrostomy combination is adapted to provide access across an abdominal wall and a stomach wall into a stomach cavity. A gastrostomy tube is provided with a channel and an axis extending between a proximal end and a distal end. An obturator disposed within the channel of the tube has a distal tip which extends beyond the distal end of the tube and is operable to penetrate the abdominal wall and the stomach wall with the gastrostomy tube. The obturator is removable from the tube leaving the gastrostomy tube operatively positioned across the abdominal wall and the stomach wall to provide access into the stomach cavity.

In another aspect of the invention, a method for placing a gastrostomy tube for operative disposition across an abdominal wall and a stomach wall to provide access into a stomach cavity, includes the steps of providing the gastrostomy tube and an obturator. The gastrostomy tube is provided with a channel extending along an axis between a proximal end and a distal end, and the obturator is provided with a distal tip. The method also includes the step of inserting the obturator into the channel of the gastrostomy tube until the distal tip of the obturator extends beyond the distal end of the tube. Then, by operation of the distal tip, the obturator and the gastrostomy tube are moved simultaneously axially through the abdominal wall and the stomach wall. Finally, the obturator is removed leaving the gastrostomy tube and its channel to provide access across the abdominal wall and the stomach wall into the stomach cavity.

In a further aspect of the invention, a method is taught for positioning a tubular axis device across a body wall, the device having a natural profile state. In accordance with this method, the device is provided with elastomeric properties and characteristics for being longitudinally stretched to a low profile state. An obturator having an operative distal tip can then be inserted into the access device where the obturator has an interference fit and the distal tip of the obturator extends distally of the access device. Stretching the axis device longitudinally moves the access device from the natural profile state to the low profile state thereby facilitating movement of the obturator and the access device through the body wall.

A further aspect of the invention involves a method for accessing, through an abdominal wall, an organ cavity defined by an organ wall. An elongate tube is provided with an axis extending between a proximal end and a distal end, the tube having at its distal end an anchor with a low profile state and a high profile state. The tube is positioned through the abdominal wall and the organ wall with the distal end of the tube disposed within the organ cavity. Expanding the anchor of the tube from the low profile state to the high profile state within the organ cavity enables the tube to be moved proximally to engage the organ wall with the anchor. The tube can then be moved to draw the organ wall to a proximal position in proximity to the abdominal wall. The organ wall is held in this proximal position with the tube providing access through the abdominal wall and the organ wall to the organ cavity.

These and other features and advantages of the invention will be more easily understood with a description of preferred embodiments and reference to the associated drawings.

DESCRIPTION OF THE DRAWINGS

FIG. 6 is a side view, partially in section of the obturator and tube in a low profile state prior to operative disposition across the abdominal wall and the stomach wall;

FIG. 8 is a side view similar to FIG. 6 showing the obturator and tube combination operatively disposed across the abdominal wall and the stomach wall with the anchor of the tube in the low profile state;

FIG. 9 is a side view similar to FIG. 8 illustrating the obturator removed from the tube and the anchor of the tube enlarged to a natural state and including a plurality of anchor snaps; and FIG. 10 is a side view similar to FIG. 9 illustrating the anchor in a high profile state maintained by the snaps, the stomach moved into proximity with the abdominal wall and this proximate position maintained by a fixation device.

DESCRIPTION OF PREFERRED EMBODIMENTS AND THE BEST MODE OF THE INVENTION

Figure 1:
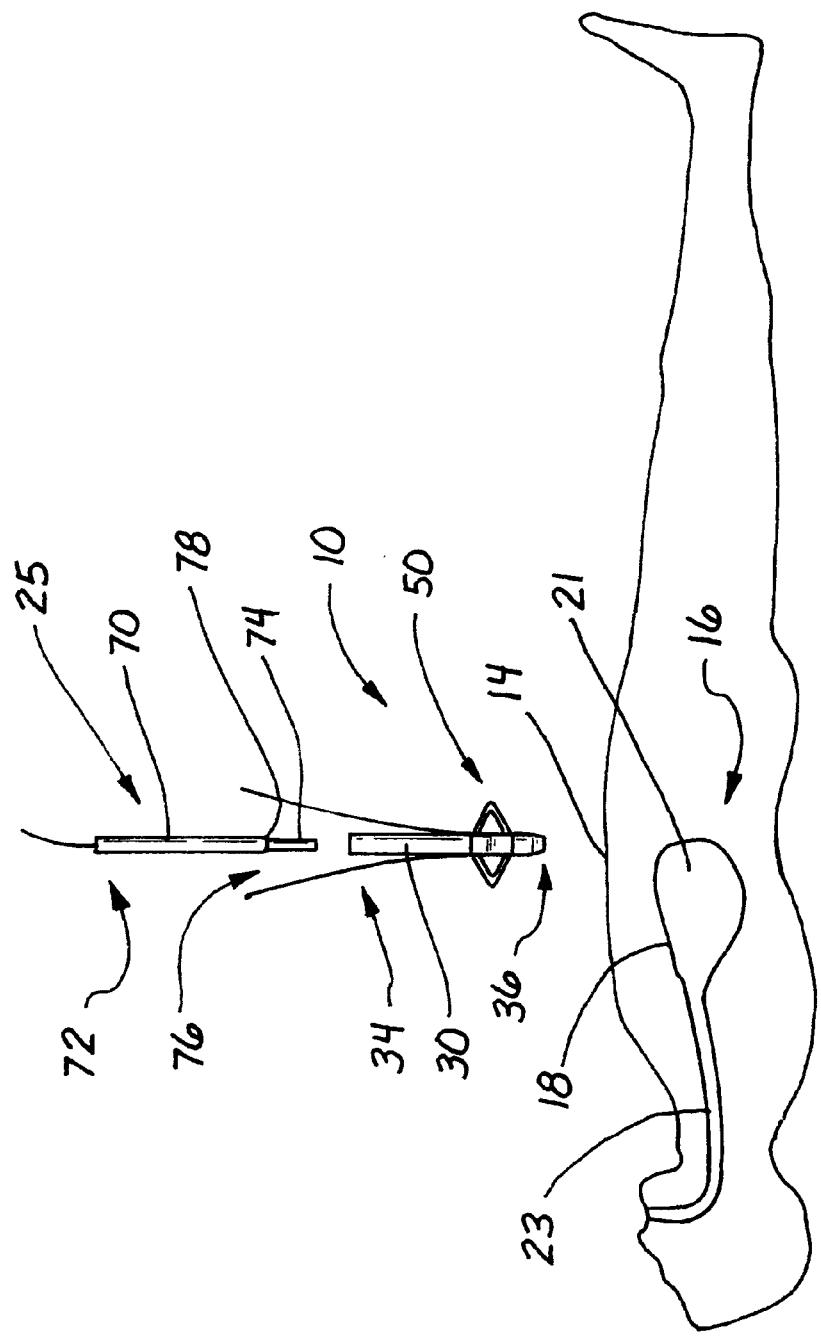
FIG. 1 is a side view of a patient showing a stomach cavity, and a gastrostomy tube and obturator associated with the present invention.

A gastrostomy tube is illustrated in FIG. 1 and designated generally by the reference numeral 10. The tube 10 is shown prior to being operatively disposed relative to a patient 12 having an abdominal wall 14, and a stomach 16 with a stomach wall 18 defining a stomach cavity 21. The stomach 16 is connected to the mouth of the patient 12 by an esophagus 23. Also illustrated in FIG. 1 is an obturator 25 which performs multiple functions relative to the G-tube 10, each of which is discussed in greater detail below.

For the reasons previously discussed, it may be desirable to position the G-tube 10 across the abdominal wall 14 and the stomach wall 18 in order to provide a feeding channel extending from outside the patient 12 into the stomach cavity 21.

Although this invention will be described relative to the G-tube 10, it will be understood that the G-tube is merely representative of many access devices which are adapted for disposition across a body wall, such as the abdominal wall 14 or stomach wall 18, in order to provide access to a body cavity, such as the stomach cavity 21. Other access devices might include, for example, catheters such as urological catheters and vein access devices such as introducers.

Figure 2:
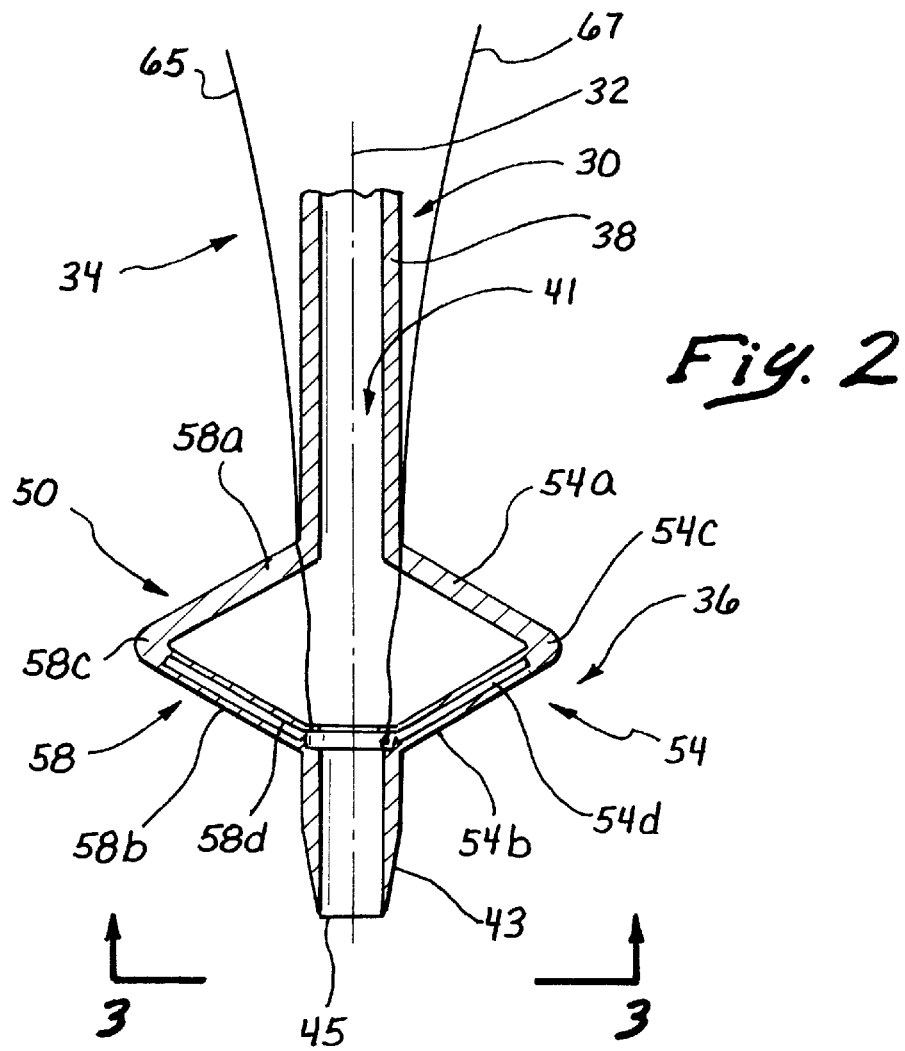
FIG. 2 is an axial cross section view of the obturator illustrated in FIG. 1.
Figure 3:
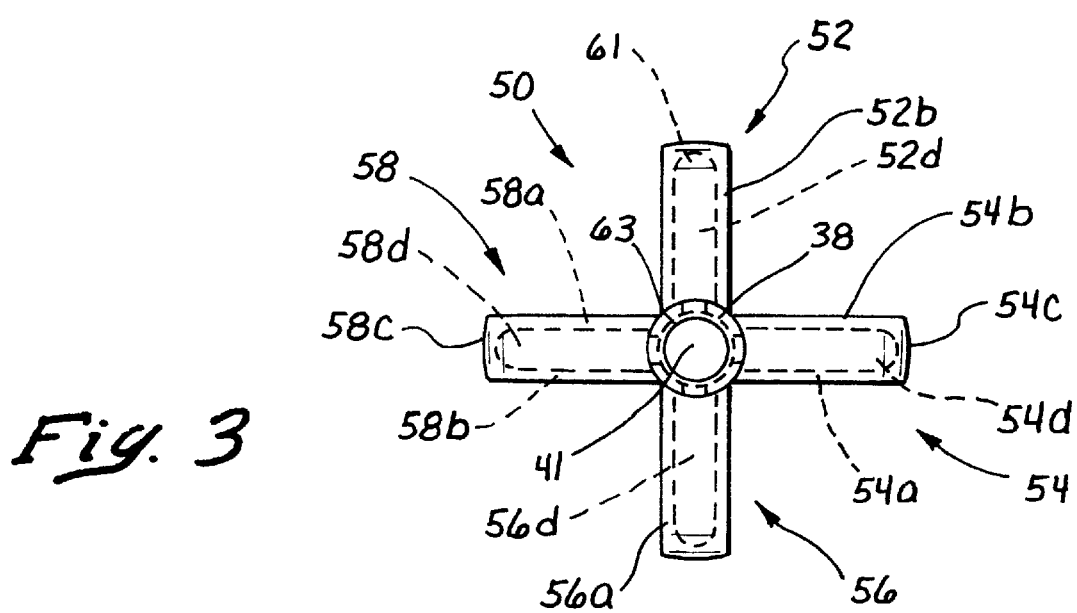
FIG. 3 is a distal end view of the obturator taken along lines 3—3 of FIG. 2.

The G-tube 10 of a preferred embodiment is best illustrated in the side view of FIG. 2 and end view of FIG. 3. It includes an elongate tubular member 30 which extends along an axis 32 between a proximal end 34 and a distal end 36. In the illustrated embodiment, the tubular member 30 has a cylindrical wall 38 which defines a working channel or, in the case of the G-tube 10, a feeding channel 41. The feeding channel 41 preferably has a cylindrical shape. At the distal end 36 of the tubular member 30, the walls 38 are provided with a radial taper 43 to form a thin circular distal edge 45.

Of particular interest of the present invention is an anchor 50 which in this case is formed integral with the walls 38 at the distal end 36 of the tubular member 30. In a particular embodiment of the G-tube 10, the tubular member 30 includes a distal section 47 at the distal end 36 which is formed distally of the anchor 50. This distal section 47 also defines a portion of the feeding channel 41. However, in this section 47, the channel 41 has a reduced diameter thereby forming a proximally facing shoulder 48.

In the illustrated embodiment, the anchor 50 is formed as a Malecot structure including multiple equally spaced expansion sections 52–58 best illustrated in FIG. 3. Each of the expansion sections 52, 54, 56 and 58 includes a proximal arm 52a, 54a, 56a and 58a, respectively, and a distal arm 52b, 54b, 56b and 58b, respectively. An elbow is formed between each associated pair of arms in the respected sections 52–58. Two such elbows, illustrated in FIG. 2, include an elbow 54c disposed between the arms 54a and 54b, and an elbow 58c disposed between the arms 58a and 58b. Living hinges are formed at each of the elbows, such as the elbows 54c and 58c, and at the junction of each of the arms 52a–58a and 52b–58b, with the wall 38 of the tubular member 30.

In a manner characteristic of the Malecot structure, these living hinges, three for each of the expansion sections of 52–58, permit the distal end 36 to be moved axially relative to the proximal end 34 with an accommodating change in the profile of the anchor 50. This capacity for axial and radial movement provides the Malecot structure with at least three profile states. A low profile state wherein the ends 34 and 36 are maximally spaced, a high profile state wherein the ends 34, 36 are minimally spaced, and a natural state (best illustrated in FIG. 2) which exists between these two extremes. These characteristics greatly facilitate the placement and anchoring of the G-tube 10 in a manner described in greater detail below.

Figure 4:
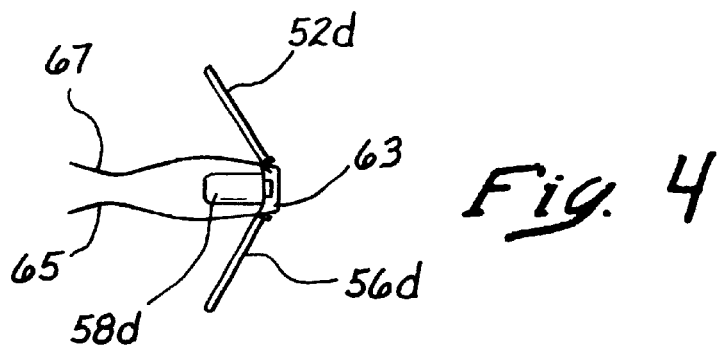
FIG. 4 is a side view of an insert which can be molded into distal arms of a Malecot structure in a preferred embodiment of the invention.
Figure 5:
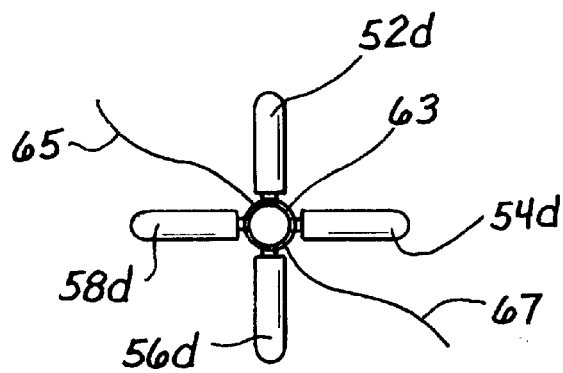
FIG. 5 is an end view of the insert illustrated in FIG. 4.

In a preferred embodiment, the G-tube 10 and anchor 50 are formed from silicone and nylon, respectively. In order to increase the structural integrity of this material, particularly in the distal arms 54a, 54b, 54c and 54d, an insert 61 can be provided. This insert 61 is illustrated in the combination of FIG. 3 and shown singularly in FIGS. 4 and 5. From these views it can be seen that the insert 61 of a preferred embodiment includes a leave 52d, 54d, 56d and 58d for each of the expansion sections 52, 54, 56 and 58. These leaves 52d–58d are bendably connected to an equally spaced round a center ring 63. In a preferred method of manufacture, the expansion sections 54–58 are insert molded around the leaves 52d–58d of the insert 61, thereby greatly reinforcing the distal arms 54b–58b.

A pair of sutures 65, 67 are attached to the distal side of the anchor 50. These sutures 65, 67 can be coupled, for example, to the distal arms 52b–58b or the associated leaves 52d–58d of the insert 61. Further advantages can be achieved when the suture 65, 67 are attached to the distal side of the anchor 50 in close proximity to the axis 32. Thus, in the illustrated embodiment, the suture 65 and 67 are connected to the ring 63 of the insert 61. The resulting structure of the G-tube 10, including the anchor 50, which may be reinforced by the insert 61, greatly facilitates placement of the G-tube 10 in the manner illustrated in FIG. 6.

Referring again to FIG. 1, it will be noted that the obturator 25 of the present invention has a cylindrical configuration with a relatively wide, large diameter section 70 at a proximal end 72, and a relatively narrow, small diameter section 74 at a distal end 76. A distally facing shoulder 78 is formed between the large diameter section 70 and the small diameter section 74. An operative tip 81, provided at the distal end 76, might be sharpened in the case of a mechanical obturator; however, in the illustrated embodiment, the tip 81 includes an electrode 83 which is electrosurgically energized.

Figure 7:
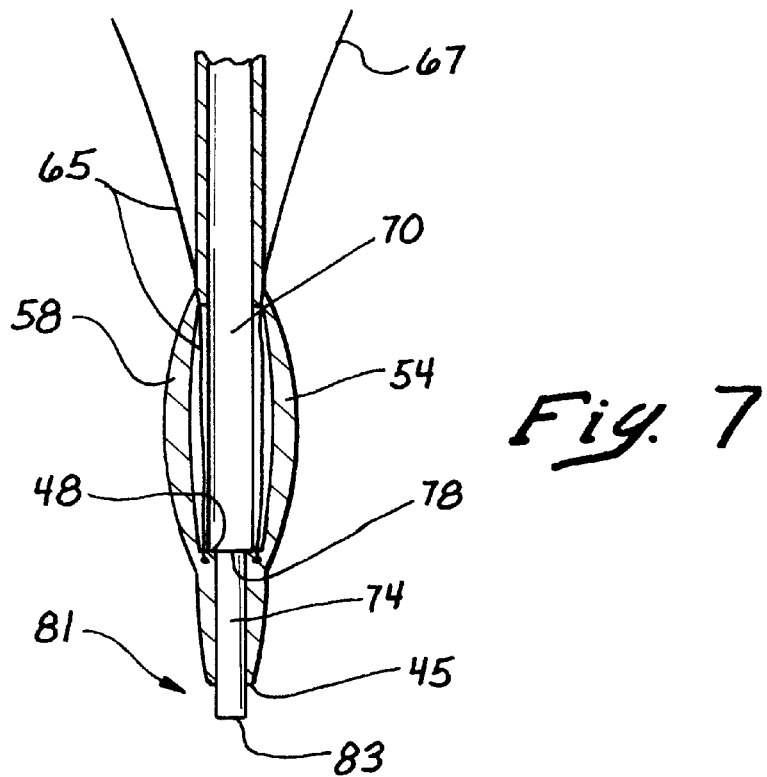
FIG. 7 is an axial cross section view of a distal end of the obturator and tube combination illustrated in FIG. 6.

Operation of the G-tube 10 and obturator 25 will be best understood with reference to FIG. 6 which shows the abdominal wall 14, the stomach wall 18, and the G-tube 10 operatively disposed with its distal end 36 in the stomach cavity 21. In accordance with a preferred method of use, the obturator 25 is initially inserted into the feeding channel 41 of the G-tube 10 until the distally facing shoulder 78 of the obturator 25 is moved into abutment with the proximally facing shoulder 48 of the G-tube 10. This is best illustrated in the enlarged cross sectional view of FIG. 7 which shows the obturator 25 operatively positioned within the G-tube 10, with the electrode 83 at the operative tip 81 disposed distally of the distal edge 45 of the G-tube 10.

This initial insertion of the obturator 25 into the G-tube 10 is performed with the anchor 50 in its natural state as best illustrated in FIG. 2. With the obturator 25 thus inserted, the user can hold the proximal end 34 of the G-tube 10 and move the obturator 25 further in the axially distal direction. Due to the interfering relationship between the shoulders 48 and 78, this results in an axial lengthening of the G-tube 10 which is accommodated by the desired radial contraction of the anchor 50. In this manner, the obturator 25 functions as a stylet to place the G-tube 10 in a low profile state as illustrated in FIG. 6. This function of the obturator 25 as a stylet can be accomplished whether the obturator is of the common mechanical type or of the electrosurgical variety illustrated.

As the resulting combination of the obturator 25 and G-tube 10 is moved axially, the electrode 83 can be energized to penetrate the abdominal 14 and stomach wall 18. It will be noted that as the obturator 25 passes through the walls 14, 18, the G-tube 10 is simultaneously moved into its operative position.

Following penetration of the walls 14, 18, the combination of the G-tube 10 and the obturator 25 will be positioned as illustrated in FIG. 8 with the distal end 36 of the G-tube 10 disposed within the stomach cavity 21 and the anchor 50 still in the low profile state. The next step in the process is to remove the obturator 25 from the G-tube 10. This is accomplished easily since the anchor 50 is biased toward the natural state illustrated in FIG. 9 from the low profile state in FIG. 8. There being no interference between the shoulders 48, 78 in the proximal direction, the obturator 25 can be axially removed with an accompanying expansion of the anchor 50 to the natural state illustrated in FIG. 9.

Once the G-tube 10 has been positioned so that it extends through the walls 14, 18 with its distal end 36 in the stomach cavity 21, it may be desirable to move the stomach 16 toward the abdominal wall 14. In the past, this has been accomplished using T-anchors which have added significantly to the complexity and complications associated with prior procedures.

In accordance with the present invention, the sutures 65, 67 are engaged externally of the patient 12 on the proximal side of the abdominal wall 14. Drawing these sutures 65, 67 proximally while holding the G-tube 10 initially results in pulling the distal arms, such as the arms 54b and 58b toward the proximal arms, such as the arms 54a and 58a. This axially compresses the anchor 50, but importantly, radially expands the anchor 50 to the high profile state illustrated in FIG. 10.

A structure which can facilitate maintenance of the anchor 50 in the high profile state includes a snap 96 which functions between associated arms, such as the arms 54a and 54b, of the anchor 50. As illustrated in the embodiment of FIG. 9, a snap projection 96e can be provided to extend inwardly of the anchor 50 from one of the arms 54a, 54b to register with an associated snap recess 96f in the opposing arm 54b, 54a. When the snap projection 96e is registered with the snap recess 96f, the associated arms, such as the arms 54a and 54b, are held in close proximity thereby maintaining the anchor 50 in the high profile state.

In the high profile state, the G-tube 10 can be moved axially, proximally to engage the stomach wall 18. Further proximal movement of the G-tube 10 draws the stomach wall 18 into juxtaposition with the abdominal wall 14.

Once this final operative position is achieved it is desirable that it be maintained. This requires not only that the anchor 50 be held in the high profile state, but also that the G-tube 10 be retained in its proximal position in order to hold the stomach wall 18 in juxtaposition against the wall 14. In accordance with a preferred embodiment and method, a fixation device is provided in the form of an annular disc 90 which can be moved axially onto the proximal end 34 and over the tubular member 30 to a location in proximity to the abdominal wall 14. Pulling the sutures 65, 67 proximally while pushing the disc 90 distally against the abdominal 14, not only maintains the anchor 50 in the high profile state, but also maintains the stomach wall 18 against the abdominal wall 14. Suture post 92 and 94 can be provided on the proximal side of the disc 90 to maintain tension on the respective sutures 65 and 67.

Realizing the high tensile forces which must be applied to the sutures 65 and 67 in order to maintain the anchor 50 in the high profile state and to maintain the wall 18 against the wall 14, one can appreciate the advantage of reinforcing the arms 54b–58b with the insert 61. Particularly, if the sutures 65 and 67 are attached to the ring 63 of the insert 61, the points of attachment between the sutures 65 and 67 and the anchor 50 can also be reinforced.

It will be appreciated that there are many aspects to the present invention any one of which may be altered within the dictates of a particular procedure. Thus, the anchor 50 of the G-tube 10 can be formed with or without the insert 61. Similarly, the obturator 25 can be of either the mechanical or electrosurgical variety and still facilitate its function as a stylet for axially expanding the G-tube 10. The G-tube 10 can be operatively positioned in combination with the obturator 25 or through a trocar or other means providing access through the walls 14, 18.

Although the suture 65, 67 are disclosed to have a dual purpose in a preferred method, they may be used to facilitate a singular function of either expanding the anchor 50 to a high profile state, or alternatively to draw the G-tube 10 proximally to a final position. In either of these cases, use of T-anchors may be desirable all within the scope of the present invention.

It is these many combinations of features and aspects of the present invention that should lead one to realize that the concept is broader than the embodiments and method steps disclosed. For this reason one is cautioned not to limit the invention to the disclosed embodiments, but rather encouraged to determine the scope of the concept only with reference to the following claims.

We claim:

1. An access device adapted for disposition across a body wall having a proximal side and an organ wall having a distal side defining an organ cavity of a patient, comprising:
   an elongate tube having an axis extending between a proximal end and a distal end, the tube being adapted to extend through the body wall and the organ wall to provide access into the body cavity;
   an anchor having a natural state facilitating insertion of the device through the body wall and a high-profile state facilitating engagement of the distal side of the organ;
   a flexible tension element coupled to the anchor and having characteristics for being tensioned on the proximal side of the body wall to move the anchor from the natural state to the high-profile state; and
   the flexible tension element being severed on the proximal side of the body wall to permit the anchor to move from the high-profile state to the natural state in order to facilitate withdrawal of the access device from the body wall.

2. The access device recited in claim 1, wherein:
   the anchor comprises a Malecot structure integral with the elongate tube; and
   the flexible tension element comprises a suture accessible on the proximal side of the body wall for expanding the Malecot structure distally of the organ wall and for drawing the Malecot structure proximally to move the organ wall into proximity with the body wall.

3. The access device recited in claim 2, wherein the Malecot structure includes:
   at least two proximal arms;
   at least two distal arms each associated with one of the proximal arms; and
   a coupling for attaching the suture to an associated one of the distal arms of the Malecot structure.

4. A gastrostomy combination adapted to provide access across an abdominal wall and a stomach wall into a stomach cavity, comprising:
   a gastrostomy tube having a channel and an a axis extending between a proximal end and a distal end;
   an obturator disposed within the channel of the gastrostomy tube and having a distal tip extending beyond the distal end of the gastrotomy tube, the distal tip of the obturator being electrically operable to penetrate the abdominal wall and the stomach wall with the gastrostomy tube; and
   the obturator being removable from the gastrostomy tube leaving the gastrostomy tube operatively positioned across the abdominal wall and the stomach wall to provide access into the stomach cavity.

5. The combination recited in claim 4, wherein the obturator is an electrosurgical obturator and the distal tip includes an electrode electrically operable to penetrate the abdominal wall and the stomach wall.

6. The combination recited in claim 5, further comprising an anchor disposed at the distal end of the gastronomy tube and operable to move between a low profile state and a high profile state;
   at least one suture fixed to the anchor and extending proximally of the tube, the suture being operable proximally of the abdominal wall to move the anchor to the high profile state within the stomach cavity, the suture being accessible exteriorally of the tube to facilitate severing the suture and to permit movement of the anchor or from the high-profile state to the natural state.

7. The access device recited in claim 1 wherein the tension element is free of any compression characteristics.

8. The access device recited in claim 7 wherein the tension element is a severable suture.

9. The access device recited in claim 7, further comprising:
   a fixation device deposed along the elongate tube on the proximal side of the wall and adapted to receive the flexible tension element in a fixed relationship with the fixation device, in order to maintain the tension on the flexible tension element and thereby hold the anchor in the high-profile state.

10. The access device recited in claim 3, further comprising:
    a snap disposed between an associated pair of the proximal arms and the distal arms, the snap having characteristics for facilitating maintenance of the anchor in the high-profile state.

11. The access device recited in claim 1 wherein the flexible tension element extends along the elongate tube exteriorly of the elongate tube from the anchor through the organ and the body wall to the proximal side of the body wall.

12. An access device adapted for disposition across a body wall having a proximal side and an organ wall having a distal side defining an organ cavity of a patient, comprising:
    an elongate tube having an axis extending between a proximal end and a distal end, the tube being adapted to extend through the body wall and the organ wall to provide access into the body cavity;
    an anchor having a low-profile state facilitating insertion of the elongate tube through the body wall, a natural state, and a high-profile state facilitating engagement of the distal side of the organ wall;
    a compression element insertable into the elongate tube to move the anchor from the natural state to the low-profile state, thereby facilitating insertion of the access device through the body wall, the compression element being removable from the elongate tube;
    a tension element coupled to the anchor and operable from the proximal side of the body wall to move the anchor from the natural state to the high-profile state thereby facilitating engagement of the distal side of the organ wall;
    a fixation element adapted to receive the tension element on the proximal side of the body wall for maintaining tension on the tension element in order to hold the anchor in the high-profile state; and
    the tension element having characteristics for being released from the fixation element in the absence of the compression element to permit movement of the anchor from the high-profile state to the natural state and thereby facilitate removal of the elongate tube from the organ and the body wall.

13. The access device recited in claim 12 wherein the compression element comprises an obturator having a distal tip sized and configured to extend distally of the anchor.

14. The access device recited in claim 13 wherein the distal tip of the obturator includes an electrosurgical electrode.

15. The access device recited in claim 12 wherein the tension element comprises at least one suture having properties for being fixed to the fixation element in order to maintain tension on the suture and to hold the anchor in the high-profile state.

* * * * *